United States Patent [19]

Debras et al.

[11] Patent Number: 4,748,291

[45] Date of Patent: May 31, 1988

[54] CATALYTIC TREATMENT PROCESS

[75] Inventors: Guy L. G. Debras, Belgrade;
Raymond M. Cahen, Bruxelles;
Georges E. M. J. De Clippeleir,
Sint-Pieters-Leeuw, all of Belgium

[73] Assignee: Labofina, S.A., Brussels, Belgium

[21] Appl. No.: 8,877

[22] Filed: Jan. 29, 1987

[30] Foreign Application Priority Data

Jan. 29, 1986 [LU] Luxembourg ............................ 87277

[51] Int. Cl.$^4$ .............................................. C07C 2/52
[52] U.S. Cl. .................................... 585/418; 585/533; 585/747
[58] Field of Search .................... 585/418, 533, 747

[56] References Cited

U.S. PATENT DOCUMENTS

| | | | |
|---|---|---|---|
| 3,702,886 | 11/1972 | Argauer et al. | 423/328 |
| 3,941,871 | 3/1976 | Dwyer et al. | 423/326 |
| 4,061,724 | 12/1977 | Grose et al. | 423/335 |
| 4,104,294 | 8/1978 | Grose et al. | 260/448 |
| 4,403,044 | 9/1983 | Post et al. | 585/418 |
| 4,414,423 | 11/1983 | Miller | 585/517 |
| 4,490,568 | 12/1984 | Garska et al. | 585/415 |
| 4,599,473 | 7/1986 | Debras et al. | 585/467 |

OTHER PUBLICATIONS

Debras et al., "Physico-Chemical Characterization of Pentasil Type Materials, I. Precursors and Calcined Zeolites" and II. Thermal Analysis of the Precursors, Zeolites, Nov. 1985, vol. 5, pp. 369–383.

*Primary Examiner*—Curtis R. Davis
*Attorney, Agent, or Firm*—William D. Jackson; John K. Abokhair; M. Norwood Cheairs

[57] ABSTRACT

A catalytic treatment process is disclosed, which is carried out under pressure, in the presence of water, and with a molecular sieve catalyst which is TEA-silicate or silicalite previously stabilized by halogenation. This process may be applied to the aromatization or to the isomerization of hydrocarbon feedstocks, and to the oligomerization of olefins. The conversion rate of the process is very stable as a function of time.

23 Claims, No Drawings

CATALYTIC TREATMENT PROCESS

The present invention relates to a catalytic treatment process which is conducted under pressure and in the presence of a catalyst comprised of a halogen stabilized TEA-silicate or silicalite. Particularly, the present invention relates to a hydrocarbon conversion process which is conducted under pressure and in the presence of TEA-silicate or silicalite which has been halogen stabilized so that the process can be conducted with less frequent regeneration or replacement of the catalyst.

Catalysts of the silicalite type or of the TEA-silicate type are relatively stable when used in catalytic processes which are conducted at atmospheric pressure. Silicalite and TEA-silicate have been used in processes such as isomerization of hydrocarbons, olefin dimerization, aromatization and reforming of paraffinic feedstocks, and more particularly such hydrocarbon conversion processes which are conducted at atmospheric pressure.

However, it is also desirable to conduct these processes at higher pressures than atmospheric pressure.

In order to operate at higher pressures while keeping the catalyst of the silicalite type reasonably stable and active, it has been proposed in U.S. Pat. No. 4,414,423 to Miller to incorporate a metal of Group IIB of the Periodic Table of the Elements, usually zinc or cadmium. The incorporation may be realized by any known method, as for instance impregnation or other usual techniques. This type of catalyst has been used in a catalytic processss for treating feedstocks containing gaseous olefins. In using the stabilized silicalite, an important decrease of the yield has been noted after a relatively short operating time. According to U.S. Pat. No. 4,414,423, it has been proposed to reduce the hourly space velocity of the feed in order to partially overcome the reduction of activity. However, if the space velocity of the feed is reduced, the plant unit must be extended in order to keep the same productivity.

TEA-silicate has been used in processes such as hydrogenation, alkylation, aromatization of hydrocarbons, and more particularly hydrocarbon conversion, insofar as the process is conducted at atmospheric pressure. For example, U.S. Pat. No. 4,490,568 to Garska et al discloses a hydrocarbon conversion process for the production of a benzene-toluene-xylene enriched stream in which the catalyst is calcined TEA-silicate. While suggesting that under special conditions the pressure may be as high as 100 atmospheres, the Garska disclosure in fact specifies that the pressure should be quite low, within the range of 0 to about 7 atmospheres, and reports only on experimental work carried out under ambient pressure conditions.

An object of the present invention is to provide a catalytic treatment process conducted under pressure and in the presence of TEA-silicate or silicalite as catalyst, which process enables the catalyst to be used for a substantial period of time.

Another object of the present invention is to provide a catalytic treatment process conducted under pressure and in the presence of TEA-silicate or silicalite catalyst which has a greater activity and is effective during longer periods of time before regeneration or replacement.

In accordance with the present invention, there is provided a process for the catalytic conversion of hydrocarbons employing a halogen stabilized catalyst. The process comprises contacting a hydrocarbon feedstream under conversion conditions which include a pressure greater than atmospheric with a catalyst in the presence of water. The catalyst comprises silicalite or TEA-silicate which has previously been stabilized by the process in which silicalite or TEA-silicate is halogenated by contacting it with a halogenating agent having a vapor pressure of at least 13 kPa at a temperature within the range of 200°–230° C. The halogenating agent is selected from the group consisting of organic saturated aliphatic chlorinated compounds, organic saturated aliphatic brominated compounds, organic saturated aliphatic fluorinated compounds, and mixtures thereof. The silicalite or TEA-silicate is contacted with the halogenating agent at a temperature within the range of 200°–500° C. for a period of time sufficient to impart a halogen concentration to the silicalite or TEA-silicate within the range of 0.1–5.0. The halogenating agent has a low hydrogen content and preferably has a ratio of halogen to carbon atoms of at least one. The halogen stabilized catalyst desirably has a halogen content within the range of 0.1–5 percent by weight and more preferably between the range of 0.1–1.0 percent by weight. Suitable conversion conditions include a temperature within the range of 250°–550° C. and a pressure within the range of $10^5$–$7 \times 10^6$ Pa. Water, which may be in the form of a liquid water or steam depending upon the reaction conditions, is supplied to the reaction zone to provide a molar ratio of water to hydrocarbons in the feedstream within the range of 0.5–1.5.

The process of the present invention is particularly suitable for olefin conversion, olefin dimerization, and aromatization of paraffinic feedstock. The feedstocks which may be used in accordance with the process of the invention are feeds comprising olefins which are gaseous at room temperature, such as for instance $C_2$, $C_3$ or $C_4$ olefins or mixtures thereof. Such olefin feedstocks may be isomerized or oligomerized. Other feeds such as $C_2$, $C_3$ or $C_4$ paraffinic hydrocarbons containing feedstocks, may also be treated in accordance with the process of the invention. Higher molecular weight paraffins or olefins such as $C_5$ and $C_6$ hydrocarbons may also be present in such feedstocks. Feedstocks coming from refining or reforming streams may also be used. These feeds are generally subjected to an aromatization reaction in order to improve their octane number. Feeds which have previously been submitted to a reforming treatment may also be used particularly where the treatment to which they have to be submitted is carried out under pressure.

The halogenated catalysts used in the process of the invention are derived from silicalite or from TEA-silicate. Silicalite is a crystalline silica polymorph which has no ion exchange capacity by comparison with zeolites. Aluminum may be present in these catalysts, but only under the form of impurities found in the starting products and particularly from the source of silica used. The methods to obtain those materials are disclosed in U.S. Pat. No. 4,061,724 to Grose and Flanigen herein incorporated by reference. Silicalites are microporous materials, hydrothermally prepared by using a reaction mixture comprising tetrapropylammonium cations, alkali metals cations, water and a source of reactive silica.

Silicalite is a highly siliceous crystalline molecular sieve. As noted above, it is prepared by the hydrothermal crystallization of silica, without added alumina, in the presence of a suitable templating agent such as tetrapropylammonium bromide. Silicalite is an intermediate pore size molecular sieve in which the silica tetrahedra forming the intracrystalline molecular sieve structure provide an average pore size within the range of 5–6.5 Å. Silicalite may be contrasted with the ZSM-5 zeolites which are characterized as aluminosilicates as disclosed in U.S. Pat. No. 3,702,886 to Argauer et al or in the case of high silica/alumina ratio (essentially aluminum-free) ZSM-5 type zeolites, as metal organosilicates as disclosed in U.S. Pat. No. Re. 29,948 (U.S. Pat. No. 3,941,871) to Dwyer et al. As noted above, silicalite is disclosed in U.S. Pat. No. 4,061,724 to Grose et al and for further description of silicalite and its method of preparation, the entire disclosure of the Grose et al patent is incorporated herein by reference. Minor amounts of aluminum, which normally will be found as an impurity in silica sources, may be present in silicalite. However, the aluminum content of silicalite is less than 1 aluminum atom for each unit cell of 96 $SiO_2$ tetrahedra. Thus the silica/alumina mole ratio of silicalite is about 200 or more.

Similarities and differences between silicalite and ZSM-5 type zeolites are examined in Debras et al "Physico-chemical characterization of pentasil type materials, I. Precursors and calcined zeolites, and II. Thermal analysis of the precursors," Nov. 1985, Vol. 5, pp. 369–383. As explained in Debras et al, the ZSM-5 materials were synthesized following the teachings of the aforementioned Argauer et al patent (termed in the paper the "A" procedure) and the silicalite materials were synthesized following the teachings of the Grose et al patent (the "G" procedure).

As disclosed in Debras et al Part I, the synthesis procedures used in the preparation of the silicalite "G" materials and the ZSM-5 zeolite "A" materials are different in several respects. The ratio of silica to the quarternary ammonium templating agent used to produce the "A" materials is much lower than the corresponding ratio used to produce the "G" materials. In addition, the $H_2O/SiO_2$ ratio for the "A" materials is substantially higher than the $H_2O/SiO_2$ ratio for the "G" materials.

Insofar as the materials themselves are concerned, the Debras et al paper reports several significant differences. All other things being equal, the average crystal size of silicalite at less than 1 aluminum atom per unit cell is greater than the average crystal size for ZSM-5 zeolite (the "A" material). Silicalite has an average crystal size greater than 5 microns. As disclosed in Debras et al at an aluminum/unit-cell ratio of less than 1, silicalite has an average crystal size of about 10 microns or more, whereas for ZSM-5 zeolites, the average crystal size is about 2 microns. The crystal sizes of the two materials are shown in FIGS. 3a and 3b of Part I of Debras et al. As further disclosed in Debras et al, ZSM-5 crystals have an aluminum rich core surrounded by an aluminum deficient outer shell. For the silicalite materials on the other hand, the core is aluminum deficient compared with the outer shell. That is, the aluminum gradient for silicalite is exactly opposite that of ZSM-5 zeolite. The aluminum gradients of the silicalite and ZSM-5 materials are shown in Table 3 and FIG. 5 of Debras et al Part I.

Silicalite in the as synthesized form and after calcining to decompose the alkyl ammonium templating agent employed in the synthesis procedure is in the orthorhombic form. However, as disclosed in U.S. Pat. No. 4,599,473 to Debras et al, silicalite of orthorhombic symmetry can be converted to monoclinic symmetry by calcining in air at a temperature of at least 600° C. for a period of 3 hours or more. Monoclinic silicalite has certain advantages in hydrocarbon conversion reactions as disclosed in the Debras et al patent. For a description of monoclinic silicalite, its preparation and use, reference is made to the aforementioned U.S. Pat. No. 4,599,473 to Debras et al the entire disclose which is incorporated herein by reference. The silicalite used in the present invention can be of orthorhombic or monoclinic symmetry.

TEA-silicate is also a crystalline silica which has no ion exchange capacity by comparison with zeolites. Aluminum may be present in these catalysts, but only under the form of impurities found in the starting products and particularly from the source of silica used. The methods to obtain those are disclosed in U.S. Pat. No. 4,104,294 to Grose and Flanigen herein incorporated by reference.

TEA-silicates are microporous materials, hydrothermally prepared by using a reaction mixture comprising tetraethylammonium cations, alkali metals cations, water and a source of reactive silica.

TEA-silicate is a distinct type of catalyst which is synthesized from a reaction system essentially free of aluminum containing reagents and which are therefore either entirely free of framework $AlO_4^-$ tetrahedra or contain no crystallographically significant amounts thereof.

TEA-silicates are disclosed U.S. Pat. No. 4,104,294. These silicates are crystalline metal organosilicates, which are prepared from a reaction system-$R_2O$ : O–8.0 $M_2O$ : 12–40/$SiO_2$ : 100–500 $H_2O$ wherein R represents the tetraethylammonium cation and wherein M represents an alkali metal cation such as sodium potassium or lithium. As indicated in the Grose et al U.S. Pat. No. 4,104,294, TEA-silicate contains the organic group in its synthesized form only, because the organic parts are eliminated by calcination before use as a hydrocarbon conversion catalyst.

The TEA-silicates used in the process of the invention may be characterized as microporous crystalline organosilicates which are hydrothermally prepared by using a reaction mixture comprising tetraethylammonium cations, alkali metal cations, water and a source of reactive silica. TEA-silicates are different from crystalline zeolites which are aluminosilicates comprising tridimensional framework of $SiO_4$ and $AlO_4$ tetrahedra linked together by oxygen atoms. The crystalline organosilicates used in the the present invention are synthesized from reaction system essentially free of aluminum containing reagents. These TEA-silicates may be prepared in accordance with the methods described in the aforementioned U.S. Pat. No.4,104,294.

The aluminum content of these compounds may vary in accordance with the amount of aluminum present as an impurity in the starting materials. For instance, the TEA-silicate catalyst employed in the present invention may have an aluminum content slightly higher than that described in the U.S. Pat. No. 4,104,294 due to aluminum impurities present in the starting materials and particularly in the solid amorphous silica used for its preparation. For example, the aforementioned patent to Grose et al refers to a molar ratio of alumina to silica of less than 0.002, corresponding to a silica/alumina ratio of 500. TEA-silicates may, however, be formulated with somewhat lower silica/alumina ratios depending upon the aluminum impurities found in the starting materials. In this regard, the aforementioned patent to Garska et al discloses TEA-silicate in which the as-synthesized product contains from about 10 to 70 moles of $SiO_2$ per 0.05 mole of $Al_2O_3$, corresponding to a silica/alumina mole ratio within the range of 200–1400. As a practical matter, the TEA-silicate employed in the present invention will have a silica/alumina mole ratio of at least 200.

These catalysts are hydrophobic and organophillic materials that are capable of absorbing neopentane, therefore indicating that they have a pore size higher than about 6.2 Å.

Where, as in the process of the present invention, conversion is conducted under superatmospheric pressure, TEA-silicate or silicalite as such are not sufficiently stable. By using a halogenated silicalite or an halogenated TEA-silicate in accordance with the present invention, excellent results are obtained with respect to life time of the catalyst, therefore enabling the process to be conducted over a longer period of time, when this process is conducted in the presence of water.

The halogen content of the catalyst depends on several factors, such as for instance the halogenation time and the type of halogenating agent. Further, in many cases, the higher the halogen content, the more stable the silicalite type catalyst.

Generally the halogen content of the silicalite or the TEA-silicate type catalyst is between about 0.1 and about 5% by weight and preferably between about 0.2 and 1.0% by weight.

The halogenated catalysts may be prepared by halogenation of TEA-silicate or silicalite at a temperature between about 200°–500° C., depending on the halogenation agent selected. This temperature is preferably between about 250°–300° C. when a chlorinated or brominated compound is used, and between about 450°–500° C. when a fluorinated compound is used.

The halogenation of the catalyst is carried out by contacting silicalite or TEA-silicate with a gaseous stream comprising the halogenating agent and a nonreducing gaseous vehicle. This treatment is carried out under specific conditions in order to obtain halogenated and stabilized catalysts which are active during long periods of time when used in processes which are conducted under pressure.

One of the conditions resides in the selection of the halogenating agent. This agent is preferably a volatile organic saturated aliphatic chlorinated, brominated or fluorinated compound, having a vapor pressure of at least 13 kPa at a temperature of about 200°–230° C. It is preferable to use a halogenated compound having a vapor pressure of about 40 to 53 kPa, or even more, in the same temperature range of 200°–230° C.

Suitable halogenating agents include volatile halogenated compounds having an halogen/carbon atomic ratio equal to or higher than 1, containing from 1 to 4 carbon atoms and which may contain oxygen. Halogenating agents, particularly suitable for producing the catalysts used in the invention include the halogenated paraffins containing from 1 to 4 carbon atoms and the halogenated ethers containing from 2 to 4 carbon atoms and which fulfill the hereabove conditions regarding volatility and number of halogen atoms. Typical examples of preferred halogenated paraffins include carbon tetrachloride, carbon tetrabromide, carbon tetrafluoride, chloroform, bromoform, fluoroform, hexachloroethane, pentachloroethane and $CH_2F_2$. Other halogenating agents include di-trichloromethyl ether, di-pentachloroethyl ether, and their brominated analogs.

Among the hereinabove cited compounds, carbon tetrachloride and di-trichloromethyl ether are particularly suitable as halogenating agents, while molecular chlorine or bromine together with hydrogen chloride or hydrogen bromide are less effective.

The non-reducing gaseous vehicle which may be used is generally nitrogen, carbon dioxide, oxygen or mixtures thereof.

The total amount of halogenating agent used and the contact time with the silicalite or TEA-silicate are also adjusted in order to produce catalysts containing from about 0.1 to about 5% by weight of chlorine and/or bromine and/or fluorine. The necessary contact time depends on various factors such as the number of halogen atoms within the halogenating agent and the concentration of halogenating agent in the gaseous stream, or the vapor pressure of said agent. Generally, the contact time is between ½ hour and 96 hours, more particularly between 1 and 12 hours. The preferred halogen content in the catalyst depends on various factors. In most cases, the higher the activity of the catalyst, the higher the halogen content.

A preferred stabilized catalyst for use in the invention has a halogen content between 0.1 and 1% by weight of the silicalite or the TEA-silicate.

The halogenated TEA-silicate or silicalite of the present invention may be produced under any known form such as pellets, powder, beads or other suitable form. These particles may be used in fixed bed or moving bed. The catalysts of the present invention may be prepared in situ (therefore it is not necessary to recover the catalyst) or ex situ.

In any case, the catalytic treatment process of the present invention is conducted in the presence of water. A difference between zeolites and the halogenated catalysts employed in the process of the invention resides in the fact that the zeolites are deleteriously affected by the presence of water (whether in the form of steam or liquid) while the halogenated catalysts are used in the presence of water and even present an improved stability.

Generally steam or liquid water is cofed into the reactor, in a mole ratio of water/feed between 0.5 and 1.5, preferably between 0.5 and 1.

The catalytic treatment process of the present invention is generally carried out at a temperature between about 250°–550° C., and more preferably between about 300°–500° C.

The catalytic treatment process is generally conducted under a pressure between $10^5$ and $7 \times 10^6$ Pa.

More particularly, when a process for the dimerization of a $C_4$- olefin feedstock is carried out, the operating conditions generally comprise a temperature between about 300° C. and about 500° C. and a pressure between about $2.10^5$ and $6.10^6$ Pa together with an amount of water such that the molar ratio water/feed is between 0.6 and 0.9. The process is carried out at a relatively high liquid hourly space velocity (LHSV), between about 5 and 200 $hr^{-1}$. These velocities depend on the type of feed to be treated, on the temperature within the reactor and on the type of desired product.

While the reasons of the efficacy of the catalytic treatment process of the invention conducted under pressure, are not known, it has been found particularly suitable for use in the dimerization and the isomerization of hydrocarbon feedstocks which contain normally gaseous olefins, insofar as the operating conditions hereabove indicated are fulfilled.

The catalysts of the halogenated silicalite type or the halogenated TEA-silicate type have particularly long activity when used in the presence of water. If, despite the stabilization provided by the process of the invention, it is desirable to regenerate a catalyst of the halogenated TEA-silicate type, or of the halogenated silicalite type as hereabove described, it may be regenerated in accordance with well known methods, by burning the hydrocarbon products which have been accumulated, e.g. by calcining them at temperatures between about 450°–550° C. under a nitrogen steam containing progressively increasing amounts of oxygen, until the $CO_2$ content in the effluent gaseous stream is lower than 0.1% by volume.

The following examples are given to better illustrate the process of the invention.

EXAMPLE 1

A reactor was charged with silicalite which has been heated at 500° C. during 3 hours under a nitrogen stream at a gaseous hourly space velocity (GHSV) of 500 (ml/ml.h).

After cooling at 280° C. while maintaining the nitrogen flow rate, the nitrogen stream fed to the reactor was saturated with $CCl_4$ for a period of 4 hours.

A $C_4$ hydrocarbon feed was passed on the obtained chlorinated silicalite, which contained 0.8% by weight chlorine, at a temperature of 340° C., under a pressure of $14.7 \times 10^5$ Pa, and a liquid hourly space velocity (LHSV) of 30 hr$^{-1}$. The feed composition was:

| | |
|---|---|
| 53.3% by weight of | n-butenes |
| 1.2% | isobutene |
| 44.6% | butanes |
| 0.9% | lighter hydrocarbons. |

Steam was cofed in a molar ratio water/feed of 1/1.

The values in wt. % of the n-butenes conversion and of the gasoline selectivity (hydrocarbons having a boiling point ranging between 36° C. and 200° C.) are indicated in the following table, together with the calculated gasoline yield (arrived at by multiplying conversion $\times$ selectivity).

TABLE I

| Time | Conversion | Selectivity | Yield |
|---|---|---|---|
| After 9 hours | 94.6% | 86.8% | 82.1% |
| 29 hours | 91.6 | 87.6 | 80.2 |
| 53 hours | 90.0 | 85.4 | 76.9 |
| 73 hours | 89.5 | 84.8 | 75.9 |
| 95 hours | 90.1 | 81.9 | 73.8 |
| 143 hours | 88.7 | 78.1 | 69.3 |

COMPARATIVE EXAMPLE 1

The same feed as in Example 1 together with steam in a molar ratio water/feed of 1/1, was passed over an untreated silicalite, at a temperature of 325° C. under a pressure of $14.8 \times 10^5$ Pa and at a LHSV of 41.2 hr$^{-1}$.

The following results were obtained (% by weight).

TABLE II

| | N—butene Conversion | Gasoline Selectivity | Gasoline Yield |
|---|---|---|---|
| after 12 hours | 91.6% | 65.2% | 59.7% |
| 26 hours | 87.3% | 80.7% | 70.5% |
| 52 hours | 60.7% | 80.4% | 48.8% |
| 75 hours | 20.4% | 88.6% | 18.1% |

COMPARATIVE EXAMPLE 2

The same feed as in Example 1 together with steam in a molar ratio water/feed of 0.5/1, was passed over an untreated silicalite at a temperature of 323° C., under a pressure of $14.8 \times 10^5$ Pa and at a LHSV of 31 hr$^{-1}$.

After 7 hours, the n-butenes conversion was 70.6% by weight and the gasoline selectivity was 87.8%. After 25 hours, the n-butene conversion was only 6.85%.

EXAMPLE 2

The experiment described in Example 1 was repeated, but with a molar ratio water/feed of 0.45/1.

The following results were obtained (% by weight).

TABLE III

| | N—butenes Conversion | Gasoline Selectivity | Gasoline Yield |
|---|---|---|---|
| after 10 hours | 89.2% | 80.3% | 71.6% |
| 24 hours | 88.6% | 84.1% | 74.5% |
| 54 hours | 82.0% | 81.8% | 67.1% |
| 78 hours | 79.1% | 81.1% | 64.2% |
| 97 hours | 76.2% | 79.8% | 60.8% |
| 122 hours | 66.5% | 80.4% | 53.5% |

EXAMPLE 3

A reactor was loaded with silicalite. Then the silicalite was heated to 500° C. during 3 hours under a nitrogen stream at a GHSV of 500. After cooling at 284° C. while maintaining the nitrogen flow rate, the nitrogen stream fed into the reactor was saturated with $CCl_4$ for a period of 110 minutes.

The same $C_4$ hydrocarbon feed as in Example 1 was passed over the hereabove silicalite, containing 0.4% chlorine.

The feed was passed at 340° C. under a pressure of $14.9 \times 10^5$ Pa, and at a LHSV of 30.

Steam was cofed at a molar ratio water/feed of 0.7/1.
The following results were obtained (% by weight).

TABLE IV

| | N—butenes Conversion | Gasoline Selectivity | Gasoline Yield |
|---|---|---|---|
| after 8 hours | 94.5% | 84.3% | 79.7% |
| 24 hours | 92.9% | 85.3% | 79.2% |
| 48 hours | 91.5% | 82.3% | 75.3% |
| 75 hours | 90.8% | 83.9% | 76.2% |
| 96 hours | 89.4% | 84.7% | 75.7% |
| 126 hours | 89.2% | 80.2% | 71.5% |
| 149 hours | 88.2% | 80.6% | 71.1% |
| 157 hours | 87.4% | 80.5% | 70.4% |

EXAMPLE 4

A reactor was charged with TEA-silicate. The TEA-silicate was heated at 500° C. during 3 hours under a nitrogen stream at a gaseous hourly space velocity (GHSV) of 500 ml/ml per hour.

After cooling at 278° C. while maintaining the nitrogen flow rate, the nitrogen stream fed to the reactor was saturated with $CCl_4$ for a period of 110 minutes.

A $C_4$ hydrocarbon feed having the same composition as that described in Example 1 was passed on the obtained chlorinated TEA-silicate, which contained 0.4% by weight chlorine, at a temperature of 380° C., under a pressure of $15.0 \times 10^5$ Pa, and a liquid hourly space velocity (LHSV) of 30 hr$^{-1}$. Steam was cofed in a molar ratio water/feed of 0.7/1.

The values (expressed in % by weight) of the n-butenes conversion and of the gasoline selectivity (hydrocarbons having a boiling point ranging between 36° C. and 200° C.) are indicated in the following table, together with the calculated gasoline yield.

TABLE V

| Time | Conversion | Selectivity | Yield |
|---|---|---|---|
| After 9 hours | 93.3% | 84.4% | 78.7% |
| 25 hours | 89.0% | 85.1% | 75.5% |
| 59 hours | 85.6% | 85.1% | 72.8% |
| 83 hours | 84.2% | 83.6% | 70.4% |

COMPARATIVE EXAMPLE 3

The same feed as Example 1 together with steam in a molar ratio water/feed of 0.74 was passed over an untreated TEA-silicate, at a temperature of 580° C. under a pressure of $15.0 \times 10^5$ Pa and LHSV of 30.2.

The following results were obtained (% by weight).

TABLE VI

| | N—butene Conversion | Gasoline Selectivity | Gasoline Yield |
|---|---|---|---|
| after 9 hours | 88.4% | 86.8% | 76.7% |
| 27 hours | 74.5% | 84.3% | 62.8% |
| 51 hours | 55.3% | 85.6% | 47.3% |
| 75 hours | 42.7% | 86.2% | 36.8% |

Having described specific embodiments of he present invention, it will be understood that modification thereof may be suggested to those skilled in the art, and it is intended to cover all such modifications as fall within the scope of the appended claims.

We claim:

1. A process for the catalytic conversion of hydrocarbons which comprises contacting a hydrocarbon feedstream under conversion conditions, including a pressure greater than atmospheric with a molecular sieve catalyst in the presence of water, said catalyst comprising silicalite or TEA-silicate which has previously been stabilized by the process comprising halogenating silicalite or TEA-silicate by contacting said silicalite or TEA-silicate with a halogenating agent having a vapor pressure of at least 13 kPa at a temperature within the range of 200°-230° C., said halogenating agent selected from the group consisting of organic saturated aliphatic chlorinated compounds, organic saturated aliphatic brominated compounds, and organic saturated aliphatic fluorinated compounds and mixtures thereof, and contacting said silicalite or TEA-silicate at a temperature within the range of 200°-500° C. for a period of time sufficient to impart a halogen concentration to said silicalite or TEA-silicate within the range of 0.1-5.0 wt. %.

2. The process of claim 1 wherein said conversion conditions include a temperature within the range of 250°-550° C. and a pressure within the range of $10^5$-$7 \times 10^6$ Pa and in the presence of water in an amount to provide a molar ratio of water to hydrocarbon feed within the range of 0.5-1.5.

3. The process of claim 1 wherein said hydrocarbon feedstock contains paraffinic hydrocarbons, or olefinic hydrocarbons, or mixtures thereof.

4. The process of claim 3 wherein said feedstock contains paraffinic hydrocarbons and said conversion reaction involves the aromatization of said paraffinic hydrocarbons.

5. The process of claim 3 wherein said conversion reaction involves the isomerization of hydrocarbons in said feedstock.

6. The process of claim 3 wherein said feedstock contains olefinic hydrocarbons and said conversion reaction involves oligomerization of said olefinic hydrocarbons and is carried out at a temperature within the range of 300°-500° C., at a pressure within the range of $2 \times 10^5 \times 6 \times 10^6$ Pa and in the presence of water in an amount to provide a molar ratio of water to hydrocarbons in said feedstock within the range of 0.6-0.9 and at a space velocity (LHSV) within the range of 5-200 $hr^{-1}$.

7. The process of claim 1 wherein said catalyst is halogen stabilized silicalite.

8. The process of claim 7 wherein said catalyst has a halogen concentration within the range of 0.1-1.0 wt. % of said silicalite.

9. The process of claim 1 wherein said catalyst is halogen stabilized TEA-silicate.

10. The process of claim 9 wherein said catalyst has a halogen concentration within the range of 0.1-1.0 wt. % of said TEA-silicate.

11. The process of claim 1 wherein said halogenating agent is an organic saturated chlorinated aliphatic compound, an organic saturated brominated aliphatic compound, or mixtures thereof.

12. The process of claim 11 wherein the silicalite or TEA silicate is contacted with said halogenating agent at a temperature within the range of 250°-300° C.

13. The process of claim 1 wherein said halogenation agent comprises an organic saturated fluorinated aliphatic compound.

14. The process of claim 13 wherein the silicalite or TEA silicate is contacted with said halogenating agent at a temperature within the range of 450°-500° C.

15. The process of claim 1 wherein said halogenation agent has a vapor pressure of at least 40 kPa at a temperature within the range of 200°-230° C.

16. The process of claim 15 wherein said halogenating agent has a vapor pressure within the range of 40 and 53 kPa at a temperature within the range of 200°-230° C.

17. The process of claim 1 wherein said halogenating agent has a ratio of halogen atoms to carbon atoms of at least 1.

18. The process of claim 17 wherein said halogenating agent comprises a halogenated paraffin having from 1 to 4 carbon atoms.

19. The process of claim 1 wherein said halogenating agent is selected from the group consisting of carbon tetrachloride, carbon tetrabromide, carbon tetrafluoride, chloroform, bromoform, fluoroform, hexachloroethane, pentachlorethane, difluoromethane and mixtures thereof.

20. A process of claim 17 wherein said halogenation agent comprises a halogenated ether containing from 2 to 4 carbon atoms.

21. The process of claim 20 wherein the halogenation agent is selected from the group consisting of di-pentachloroethyl ether, di-trichloromethyl ether, di-pentabromoethyl ether, di-tribromomethyl ether and mixtures thereof.

22. The process of claim 1 wherein the non-reducing gas is selected from the group consisting of nitrogen, carbon dioxide, oxygen and mixtures thereof.

23. The process of claim 1 wherein the silicalite or TEA silicate is contacted with said halogenating agent for a period of time sufficient to impart a halogen concentration to said silicaliteor or TEA silicate within the range 0.1 to 1 wt. %.

* * * * *